(12) United States Patent
Ding et al.

(10) Patent No.: US 9,661,870 B2
(45) Date of Patent: May 30, 2017

(54) NANOGEL COMPRISING WATER-SOLUBLE ACTIVE INGREDIENTS

(71) Applicant: DSM IP ASSETS B.V., Heerlen (NL)

(72) Inventors: Xuzhe Ding, Shanghai (CN); Olivia Vidoni, Basel (CH); Ping Yao, Shanghai (CN)

(73) Assignee: DSM IP ASSETS B.V., Heerlen (NL)

( * ) Notice: Subject to any disclaimer, the term of this patent is extended or adjusted under 35 U.S.C. 154(b) by 8 days.

(21) Appl. No.: 14/410,325

(22) PCT Filed: Jun. 10, 2013

(86) PCT No.: PCT/IB2013/054730
§ 371 (c)(1),
(2) Date: Dec. 22, 2014

(87) PCT Pub. No.: WO2014/001932
PCT Pub. Date: Jan. 3, 2014

(65) Prior Publication Data
US 2015/0366243 A1    Dec. 24, 2015

(30) Foreign Application Priority Data

Jun. 27, 2012  (WO) ............... PCT/CN2012/000881
Oct. 10, 2012  (EP) ................................. 12187990

(51) Int. Cl.
*A23L 2/66*       (2006.01)
*A23L 1/0526*     (2006.01)
(Continued)

(52) U.S. Cl.
CPC .......... *A23L 1/0526* (2013.01); *A23K 20/147* (2016.05); *A23K 20/163* (2016.05);
(Continued)

(58) Field of Classification Search
None
See application file for complete search history.

(56) References Cited

U.S. PATENT DOCUMENTS 8,563,066 B2 * 10/2013 Sexton .................. A23G 4/06
426/2
2011/0038942 A1  2/2011 Livney
(Continued)

FOREIGN PATENT DOCUMENTS

CN  101058649      10/2011
KR  2011 0114195   10/2011

OTHER PUBLICATIONS

Yin et al. (Stable nano-sized emulsions produced from soy protein and soy polysaccharide complexes, Journal of Colloid and Interface Science 380 (2012) 51-59).*

(Continued)

*Primary Examiner* — Robert A Wax
*Assistant Examiner* — Melissa Mercier
(74) *Attorney, Agent, or Firm* — Nixon & Vanderhye P.C.

(57) ABSTRACT

The present invention relates to a nanogel composition comprising at least one water-soluble active ingredient, one or more plant proteins, and one or more soy soluble polysaccharides. These compositions can be used for the enrichment, and/or fortification of food, beverages, animal feed and/or cosmetics and allow stabilization of the active ingredient. The present invention also refers to the process for the preparation of such nanogel compositions. The present invention furthermore refers to a process for the manufacture of a beverage by mixing the compositions with ingredients of beverages. The present invention also refers to beverages obtainable by this process.

14 Claims, 2 Drawing Sheets

(51) Int. Cl.
| | |
|---|---|
| A23L 2/52 | (2006.01) |
| A61K 31/375 | (2006.01) |
| A61K 31/4188 | (2006.01) |
| A61K 31/4415 | (2006.01) |
| A61K 31/455 | (2006.01) |
| A61K 31/51 | (2006.01) |
| A61K 31/519 | (2006.01) |
| A61K 8/64 | (2006.01) |
| A61K 8/67 | (2006.01) |
| A61K 8/73 | (2006.01) |
| A61Q 19/00 | (2006.01) |
| A61K 8/02 | (2006.01) |
| A61K 8/49 | (2006.01) |
| A23K 20/174 | (2016.01) |
| A23K 20/147 | (2016.01) |
| A23K 20/163 | (2016.01) |
| A23L 29/238 | (2016.01) |
| A23L 33/10 | (2016.01) |
| A23L 33/105 | (2016.01) |
| A23L 33/15 | (2016.01) |
| A23L 33/185 | (2016.01) |
| A23L 33/21 | (2016.01) |

(52) U.S. Cl.
CPC ............. *A23K 20/174* (2016.05); *A23L 2/52* (2013.01); *A23L 2/66* (2013.01); *A23L 29/238* (2016.08); *A23L 33/10* (2016.08); *A23L 33/105* (2016.08); *A23L 33/15* (2016.08); *A23L 33/185* (2016.08); *A23L 33/21* (2016.08); *A61K 8/0241* (2013.01); *A61K 8/4953* (2013.01); *A61K 8/645* (2013.01); *A61K 8/67* (2013.01); *A61K 8/73* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61Q 19/00* (2013.01); *A23V 2002/00* (2013.01); *A61K 2800/10* (2013.01); *A61K 2800/413* (2013.01)

(56) References Cited

U.S. PATENT DOCUMENTS

2012/0093933 A1    4/2012  Livney et al.
2012/0288533 A1*  11/2012  Livney ..................... A23L 2/52
                                                                    424/400

OTHER PUBLICATIONS

International Search Report for PCT/IB2013/054730 mailed Sep. 25, 2013.
D. Renard et al., Biopolymeric Colloidal Carriers for Encapsulation or Controlled Release Applications, International Journal of Pharmaceuticals, vol. 242, No. 1-2, pp. 163-166.
L. Chen et al., "Chitosan/Beta-lactoglobulin Core-Shell Nanoparticles as Nutraceutical Carriers", vol. 26, No. 30, Oct. 1, 2005, pp. 6041-6053.
B. Bae et al., "Self-Quenching Polysaccharide-Based Nanogels of Pullulan/folate-photosensitizer Conjugates for Photodynamic Therapy", vol. 31, No. 24, Aug. 1, 2010, pp. 6325-6335.
Chinese Office Action for application 201380033849.2 mailed Sep. 15, 2015, 12 pages.
Jingbo Liu et al., "Theories of functional foods," Chemical Industry Press, $1^{st}$ version Feb. 2008, pp. 103-104 and 111-112.
Maeda, H.; Journal of The Japanese Society for Food Science and Technology. 47(2000) 338-338.
Nakamura et al, Biosci. Biotech. Biochem. 65 (2001) 2249-2258.
Nakamura, A. et al., J. Agric. Food Chem. 52 (2004) 5506-5512.
Jones, O.G. et al; Comprehensive Reviews in Food Science and Food Safety 9(2010) 374-397.
Chen, L.Y. et al; Trends in Food Science & Technology 17(2006) 272-283.
Zúñiga, R.N. et al; Trends in Food Science & Technology, 19 (2008) 176-187.

* cited by examiner

NANOGEL COMPRISING WATER-SOLUBLE ACTIVE INGREDIENTS

This application is the U.S. national phase of International Application No. PCT/IB2013/054730 filed 10 Jun. 2013 which designated the U.S. and claims priority to PCT/CN2012/000881 filed 27 Jun. 2012, and CN 12187990.2 filed 10 Oct. 2012, the entire contents of each of which are hereby incorporated by reference.

The present invention relates to a nanogel composition comprising at least one water-soluble active ingredient, one or more plant proteins, and one or more soy soluble polysaccharides. These compositions can be used for the enrichment, and/or fortification of food, beverages, animal feed and/or cosmetics and allow stabilization of the active ingredient. The present invention also refers to the process for the preparation of such nanogel compositions. The present invention furthermore refers to a process for the manufacture of a beverage by mixing the compositions with ingredients of beverages. The present invention also refers to beverages obtainable by this process.

Compositions to enrich or fortify food, beverages, animal feed or cosmetics which contain water-soluble active ingredients, for example folic acid, are known in the art (S. M. Lopera et al. (2009), Vitae 16, p 55-65). Alginate beads have been used in microencapsulation of folates because they are easy to prepare on lab scale, it is mild hydrogelling process and relatively safe for use into food formulations (K. Kasipathy, 2008, Delivery and controlled release of bioactives in foods and nutraceuticals, Chapter 13, p. 331-341). However, alginate microcapsules have a porous nature leading to leakages of folic acid and moderate stability of folic acid when exposed to light and in acidic conditions typical of beverages (pH 3 to 5). Indeed, folic acid is well known for its instability (cleavage of the C9-N10 bond) when exposed to ultraviolet radiation. Moreover, folic acid is poorly soluble at the pH range of acidic beverages in the range of pH 2 to 4.

Therefore, there is still a need for compositions comprising water-soluble active ingredients for the enrichment, and/or fortification of food, beverages, animal feed, or cosmetics which do not show the above-mentioned problems.

It was therefore an object of the present invention to provide compositions of water-soluble active ingredients having the desired properties as indicated above, e.g. very good properties referring to stability of the active ingredient in acidic pH (3 to 5), stability of the active ingredient when exposed to light (photostability), and optical clarity when used in a beverage. It was also an objective of the invention to improve the process for the preparation of compositions of water-soluble active ingredients.

This objective has been solved by a nanogel composition comprising:
  a) 0.1 to 5 weight-% based on the dry weight of the composition of at least one water-soluble active ingredient selected from ascorbic acid, biotin, folic acid, nicotinic acid, thiamine, and vitamin B6;
  b) 9 to 40 weight % based on the dry weight of the composition of one or more plant protein(s) chosen from the group of proteins suitable for food application; and
  c) 50 to 90 weight-% based on the dry weight of the composition of one or more soy soluble polysaccharide(s);

wherein the weight ratio of protein(s) to polysaccharide(s) based on the composition in dry matter is chosen like 1:b with the proviso that b is comprised between 1 and 6.

The term "nanogel" in the present invention refers to a nanoparticle composed of a cross-linked hydrophilic hetero polymer network (hydrogel).

Water-soluble active ingredients suitable for the composition according to the present invention are water-soluble active ingredients having a pKa ranging from 4 to 6 and are preferably selected from ascorbic acid (Vitamin C, pKa 4.17); biotin (Vitamin B8, pKa 5.33); folic acid (Vitamin B9, pKa 4.7); nicotinic acid (niacin or vitamin B3, pKa 4.9); thiamine (vitamin B1, pKa 4.8); vitamin B6, pKa 5.33, as well as mixtures thereof. Most preferred water-soluble active ingredient for all the embodiments of the present invention is folic acid.

According to the present invention preferred plant protein(s) are derived from soy, lupin (e.g. *L. albus, L. angustifolius* or varieties thereof), pea and/or potato. The proteins may be isolated from any part of the plant, including fruits (like e.g. soy beans), seeds (including prepared or processed seeds) and the like; or from whole flour or defatted products such as shred, flakes etc.

For the composition of the present invention, especially preferred are soy and pea protein, even more preferred soy protein is "acid soluble soy protein" (Soyasour 4000K, with a protein content greater or equal to 60 weight-%). Most preferred is Soyasour 4000K, with a protein content greater or equal to 80 weight-%, moisture, below or equal to 7.5 weight-%, fat below or equal to 1.5 weight-%, pH 3.6 to 6.4) It can be sourced from Jilin Fuji Protein Co. Ltd. Preferred Pea protein source is from Cosucra SA (Warcoing, Belgium)

The term "soy soluble polysaccharide" as used herein refers to Soy soluble polysaccharide with a content greater or equal to 60 weight-% polysaccharides. Most preferred soy soluble polysaccharide is soy soluble polysaccharide with a content greater or equal to 70 weight-% polysaccharides, smaller or equal to 10 weight-% protein, smaller or equal to 1 weight-% fat, smaller or equal to 8 weight-% moisture, smaller or equal to 8 weight-% ash, and a pH comprised between 3 to 6. It can be sourced from Fuji Co., Ltd.

For the composition according to the present invention, it is preferred to choose the weight ratio of protein(s) to polysaccharide(s) based on the composition in dry matter like 1:b with the proviso that b is comprised between 1 and 5, especially preferred b is comprised between 2 and 4, even more preferred, b is 3.

In an especially preferred embodiment of the present invention, the average particle size of the nanogel is between 120 and 250 nm as measured by dynamic light scattering.

The invention also relates to a process for the manufacture of a stable nanogel composition as indicated above comprising the following steps (the process can be carried out using the ingredients in amounts as specified herein):
  I) mixing in water one or more soy-soluble polysaccharide(s) as a solution at pH around 7.4 with a solution of at least one water-soluble active ingredient selected from ascorbic acid, biotin, folic acid, nicotinic acid, thiamine, and vitamin B6; and a solution of plant protein(s), wherein the concentration of soy protein is from 1 to 10 g/l, the weight ratio of protein to polysaccharide is from 1:1 to 1:6, and the concentration of water-soluble active ingredient is between 0.02 and 0.2 g/l,
  II) optionally stirring the mixture of step I) for 1 minute to 8 hours;

III) adjusting the pH of the mixture from step I) or II) to pH around 4, and repeat the pH adjustment after 2 to 3 hours;
IV) homogenizing the mixture of step III) with a conventional homogenization process known to the person skilled in the art followed by heating at 90° C. for 1 hour;
V) heating the nanogel at a temperature comprised between 70 to 95° C., for at least 45 minutes;
VI) optionally drying the resulting nanogel of step V).

According to the present invention preferred proteins are plant proteins as described above.

In a preferred embodiment, the concentration of plant protein(s) is from 4 to 6 g/l. The preferred weight ratio of protein to polysaccharide is from 1:2 to 1:4, even more preferred is 1:3. The concentration of water soluble active ingredient is preferably between 0.01 and 0.15 g/l, and the preferred water-soluble active ingredient is folic acid.

The repeated pH adjustment to pH around 4 in step III) can be performed by any acid which is allowed in food, and preferably hydrochloric acid is used.

The homogenization of step IV) can be performed by any homogenization process known to the person skilled in the art like ultrasonication or high pressure homogenization.

Ultrasonication generates alternating low-pressure and high-pressure waves in liquids, leading to the formation and violent collapse of small vacuum bubbles. This phenomenon, called cavitation, causes high speed impinging liquid jets and strong hydrodynamic shear-forces, combined with compression, acceleration, pressure drop, and impact, causing the disintegration of particles and dispersion throughout the product as well as the mixing of reactants. (Encyclopedia of emulsion technology, 1983, Vol 1, P. Walstra, page 57, Ed P. Becher, ISBN: 0-8247-1876-3)

In the case of the high pressure homogenization process, the mixture is passed through a gap in the homogenizing valve; this creates conditions of high turbulence and shear, combined with compression, acceleration, pressure drop, and impact, causing the disintegration of particles and dispersion throughout the product. The size of the particles depends on the operating pressure used during the process and the type of gap selected. (Food and Bio Process Engineering, Dairy Technology, 2002, H. G. Kessler, Ed A. Kessler, ISBN 3-9802378-5-0).

The most preferred homogenization to carry out the present invention is high pressure homogenization according to (Donsi et al. J. Agric. Food Chem., 2010, 58:10653-10660) in view of the efficiency and high throughput of this technology to produce nanoemulsions. More preferably, it is performed at 500 to 700 bars for at least 1 minute, even more preferably, at 600 bars for at least 2 minutes.

The nanogel of step V) may be used as it is or dried for later use. The drying step may be carried out with any conventional drying process known to the person skilled in the art, preferred are spray drying and/or a powder catch process where sprayed suspension droplets are caught in a bed of an adsorbant such as starch or calcium silicate or silicic acid or calcium carbonate or mixtures thereof and subsequently dried.

The present invention also relates to a nanogel obtainable by a process as described above, and preferably, wherein the plant protein is soy or pea protein and the water-soluble active ingredient is folic acid.

The present invention is also directed to the use of nanogels as described above for the enrichment, and/or fortification of food, beverages, animal feed and/or cosmetics, preferably for the enrichment, and/or fortification of beverages, even more preferably acidic beverages (pH 3 to 5).

Other aspects of the invention are food, beverages, animal feed, cosmetics containing a composition as described above.

Beverages wherein the product forms of the present invention can be used as an additive ingredient can be carbonated beverages e.g., flavored seltzer waters, soft drinks or mineral drinks, as well as non-carbonated beverages e.g. flavored waters, fruit juices, fruit punches and concentrated forms of these beverages. They may be based on natural fruit or vegetable juices or on artificial flavors. Also included are alcoholic beverages and instant beverage powders. Besides, sugar containing beverages diet beverages with non-caloric and artificial sweeteners are also included.

Further, dairy products, obtained from natural sources or synthetic, are within the scope of the food products wherein the product forms of the present invention can be used as a nutritional ingredient. Typical examples of such products are milk drinks, ice cream, cheese, yogurt and the like. Milk replacing products such as soymilk drinks and tofu products are also comprised within this range of application.

Also included are sweets which contain the product forms of the present invention as an additive ingredient, such as confectionery products, candies, gums, desserts, e.g. ice cream, jellies, puddings, instant pudding powders and the like.

Also included are cereals, snacks, cookies, pasta, soups and sauces, mayonnaise, salad dressings and the like which contain the product forms of the present invention as a colorant or a nutritional ingredient. Furthermore, fruit preparations used for dairy and cereals are also included.

The final concentration of the one or more water-soluble active ingredients, preferably folic acid, which is added via the compositions of the present invention to the food products may preferably be from 0.1 to 50 ppm, particularly from 1 to 30 ppm, more preferred 3 to 20 ppm, e.g. about 6 ppm, based on the total weight of the food composition and depending on the particular food product to be fortified and the intended level of fortification.

The food compositions of this invention are preferably obtained by adding to a food product the water-soluble active ingredient in the form of a composition of this invention. For fortification of a food product a composition of this invention can be used according to methods per se known for the application of water dispersible solid product forms.

In general the composition may be added either as an aqueous stock solution, a dry powder mix or a pre-blend with other suitable food ingredients according to the specific application. Mixing can be done e.g. using a dry powder blender, a low shear mixer, a high-pressure homogenizer or a high shear mixer depending on the formulation of the final application. As will be readily apparent such technicalities are within the skill of the expert.

The invention also relates to a process for the manufacture of a beverage comprising the steps of homogenizing the composition according to the present invention, and mixing 1 to 50 ppm based on the water-soluble active ingredient content, preferably 5 ppm of the emulsion with further usual ingredients of beverages.

Further, the present invention relates to beverages obtainable by the process for the manufacture of a beverage as described above. Preferably the beverage has a pH comprised between 2 and 8, more preferably, between 3 and 5.5.

The present invention is further illustrated by the following examples, which are not intended to be limiting.

EXAMPLES

Example 1

Interaction of Folic Acid with Soy Protein, Soy Polysaccharide, or Soy Protein/Soy Polysaccharide Complex Nanogel at pH 7.4

Soy protein is from Jilin Fuji Protein Co. Ltd. (Soyasour 4000K, acid soluble soy protein; ASSP) with protein content 88% (dry basis). It has an isoelectric point around pH 4.7. Soy soluble polysaccharides (SSP) with 70 to 80 weight-% polysaccharides were sourced from Fuji Co., Ltd.

Figure 1:
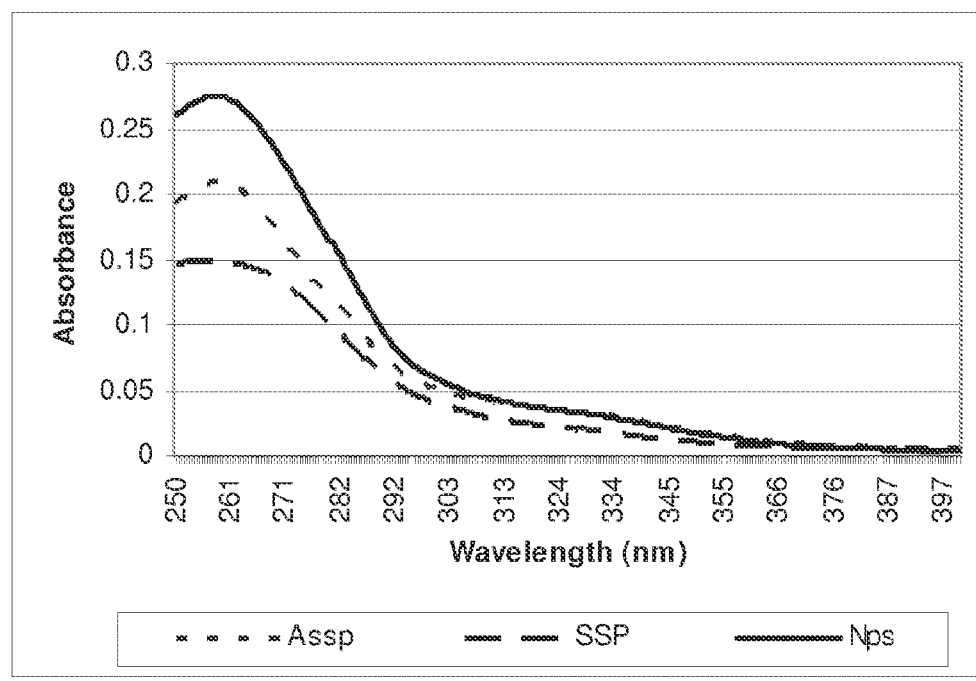
FIG. 1 shows the UV spectra of individual protein (Assp), individual polysaccharide (SSP) and protein/polysaccharide complex nanogel (Nps) solutions after ultrafiltration.

Considering the solubility of folic acid, the interaction at pH 7.4 was investigated. The individual protein solution, individual polysaccharide solution, and the protein/polysaccharide complex nanogel solution were adjusted to pH 7.4 first. Then the folic acid, dissolved in 10 mM phosphate buffer pH 7.4, was added and the mixture was incubated under stirring at room temperature overnight. The final protein concentration in the mixture was 4 mg/ml and polysaccharide concentration was 12 mg/ml. The free folic acid in the mixture was isolated by a high-flow ultrafiltration membrane (cutoff molecular weight 3 kDa, MicroconYM-3, Millipore), and was collected in the ultrafiltrate. Individual folic acid solution was also passed through the ultrafiltration membrane; 97% of the folic acid (Table 1) in the ultrafiltrate confirms the recovery of the folic acid. The individual protein, individual polysaccharide, and protein/polysaccharide complex nanogel solutions were also passed through the ultrafiltration membrane; their UV spectra of the ultrafiltrates (FIG. 1) show the absorbance at UV region, indicating small peptides in the ultrafiltrates. The FA concentration in the ultrafiltrate was calculated by deducting the 280 nm absorbance shown in FIG. 1 from the 280 nm absorbance of the ultrafiltrate. Table 1 shows that about 10% of the FA binds to the protein or nanogel; almost no folic acid binds to the polysaccharide at pH 7.4.

TABLE 1

Free folic acid (FA) concentration in different mixtures at pH 7.4. The free folic acid in the mixture was isolated by ultrafiltration.

| Sample | FA concentration in feed (mM) | FA concentration in ultrafiltration (mM) | Recovered FA in ultrafiltration (%) |
|---|---|---|---|
| Protein + FA | 0.25 | 0.215 ± 0.005 | 86 ± 2 |
| | 0.5 | 0.435 ± 0.005 | 87 ± 2 |
| Polysaccharide + FA | 0.25 | 0.241 ± 0.01 | 96 ± 4 |
| | 0.5 | 0.506 ± 0.01 | 101 ± 2 |
| Protein/polysaccharide nanogel + FA | 0.25 | 0.228 ± 0.005 | 89 ± 2 |
| | 0.5 | 0.447 ± 0.01 | 89 ± 2 |
| FA | 0.5 | 0.485 ± 0.01 | 97 ± 2 |

Example 2

Interaction of Folic Acid with Soy Protein, Soy Polysaccharide, or Soy Protein/Soy Polysaccharide Complex Nanogel at pH 4

The nanogels are relatively hydrophobic at pH 4 characterized by pyrene fluorescence, folic acid is also a hydrophobic compound at pH 4. Therefore, the nanogels may bind folic acid via hydrophobic interaction. Considering the pH dependent solubility, folic acid was added into weight ratio 1:3 nanogel solution in 3 different methods as follows.

(1) The weight ratio 1:3 nanogel solution was adjusted to pH 7.4 and then solid folic acid was added to reach final folic acid concentration 1 mM, protein concentration 4 mg/ml, and polysaccharide concentration 12 mg/ml. After overnight stirring to dissolve the folic acid, the mixture was changed to pH 4.0.

(2) Folic acid was dissolved in 10 mM pH 7.4 phosphate buffer. The folic acid solution was added dropwise into the nanogel solution with pH 4.0 to reach folic acid concentration 0.25, 0.5, or 1 mM, followed by overnight stirring. The pH of the mixture was about 4.0.

(3) Folic acid was dissolved in 10 mM pH 7.4 phosphate buffer. The nanogel solution was adjusted to pH 7.4. The folic acid solution was mixed with the nanogel solution to reach folic acid concentration 0.1, 0.5, or 1 mM, after overnight stirring, the pH of the mixture was adjusted to 4.0.

Yellow precipitates of folic acid appeared at pH 4.0 after short-time storage for all the mixtures above. The same yellow precipitates were also observed for the mixtures of folic acid with individual protein and individual polysaccharide. For the individual protein, the supernatant presents yellow colour, whereas the others are colourless. These results indicate that at pH 4.0, the protein can bind/stabilize a part of the folic acid, the nanogel and soy polysaccharide can bind/stabilize folic acid barely.

Example 3

Folic Acid/Soy Protein/Soy Polysaccharide Nanogel Preparation

Because the soy protein can bind a part of folic acid at pH 4 but the nanogels cannot, folic acid/protein/polysaccharide nanogels were prepared by mixing folic acid with the protein and polysaccharide at pH 7.4, followed by pH adjustment, high pressure homogenization, and heating. Following is the details of the preparation: 7.88 g soy polysaccharide solution with 50 mg/ml concentration was added into 5 ml water, followed by adding 6.25 ml 1 mM pH 7.4 folic acid solution and 6.25 ml soy protein solution with 20 mg/ml concentration under stirring. In the mixture, the final protein concentration was 5 mg/ml, polysaccharide concentration 15 mg/ml, folic acid concentration 0.25 mM, and the volume was 25 ml. The pH of the mixture was adjusted to 4.0, after 3 h stirring, the pH was adjusted to 4.0 again. The mixture was homogenized by high pressure homogenization at 600 bar for 2 min and then was heated at 90° C. for 1 h to obtain folic acid encapsulated soy protein/soy polysaccharide nanogels. Individual protein and individual polysaccharide were also used to prepare folic acid/protein nanogels and folic acid/polysaccharide nanogels using this method.

Figure 2:
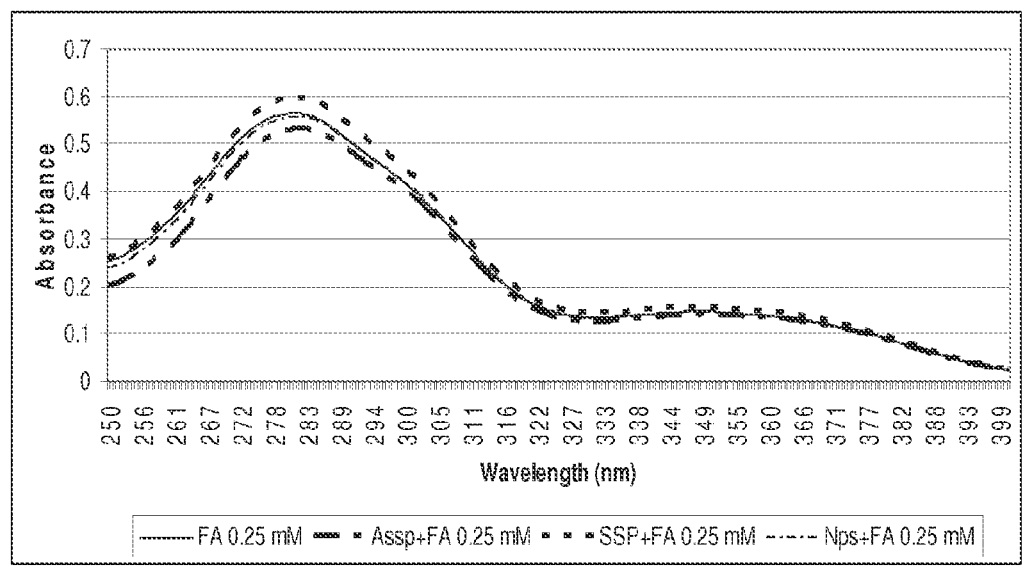
FIG. 2 shows UV-spectra of the released folic acid from folic acid/protein/polysaccharide nanogels, folic acid/polysaccharide nanogels, and folic acid/protein nanogels at pH 7.4. The released folic acid was isolated by ultrafiltration. The folic acid solutions prepared at pH 7.4 directly were used as controls.
Figure 2:
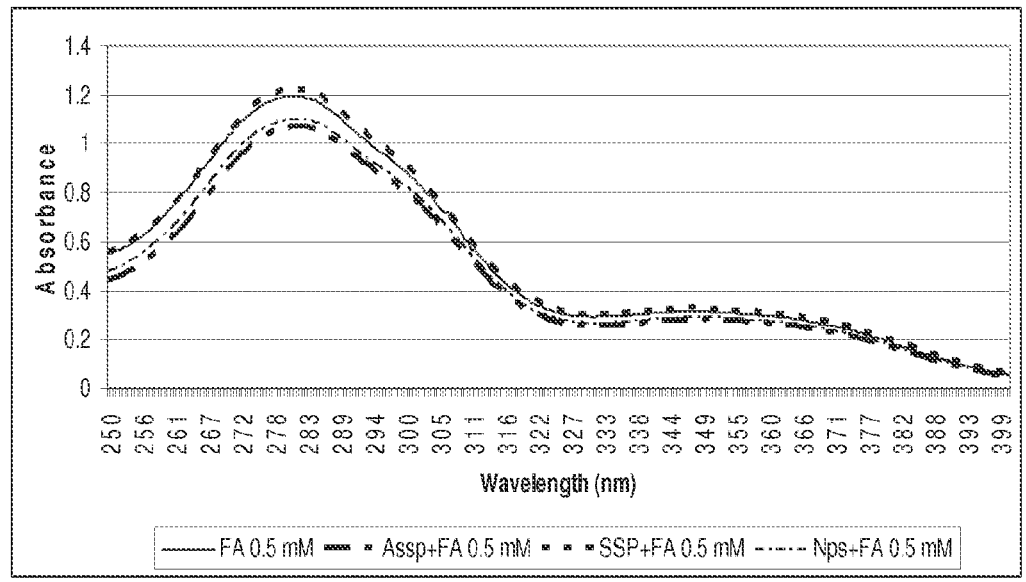

The resultant folic acid/protein/polysaccharide nanogel solution, folic acid/protein nanogel solution, and folic acid/ polysaccharide nanogel solution were changed to pH 7.4 to release folic acid from the nanogels; the released folic acid was isolated by ultrafiltration. The folic acid concentration in the ultrafiltrate was measured as described above and the 0.25 and 0.5 mM folic acid solutions prepared at pH 7.4 directly were used as the controls. The result in FIG. 2 shows that the folic acid spectra do not change after mixing, pH adjusting, homogenization, and heating process. The intensity decreases for the mixture containing protein or nanogels, consistent with the result of the folic acid binding at pH 7.4 (Table 1), i.e., about 10% FA bound with the protein and nanogels.

Example 4

Stability of Folic Acid/Soy Protein/Soy Polysaccharide Nanogels

Dynamic light scattering (DLS) was performed to measure the size of folic acid/protein/polysaccharide nanogels at pH 4.0. The data in Table 2 show that the nanogels with folic acid concentration of 0.25 and 0.5 mM have similar size as the nanogels without folic acid. After 1 month of storage, the nanogels do not change their size.

TABLE 2

DLS result of FA/protein/polysaccharide nanogels with folic acid (FA) concentration of 0.25 and 0.5 mM. The protein/polysaccharide nanogels were used as controls.

| Nanogel sample | FA concentration in the nanogels (mM) | Storage time | $D_h$ (nm) | PDI |
|---|---|---|---|---|
| Protein/ polysaccharide | 0 | Fresh prepared | 178 ± 2 | 0.16 ± 0.01 |
| FA/protein/ polysaccharide | 0.25 | | 170 ± 4 | 0.13 ± 0.02 |
| FA/protein/ polysaccharide | 0.5 | | 175 ± 1 | 0.12 ± 0.02 |
| Protein/ polysaccharide | 0 | 2 weeks | 183 ± 1 | 0.17 ± 0.01 |
| FA/protein/ polysaccharide | 0.25 | | 173 ± 2 | 0.14 ± 0.03 |
| FA/protein/ polysaccharide | 0.5 | | 175 ± 1 | 0.12 ± 0.02 |
| Protein/ polysaccharide | 0 | 1 month | 181 ± 1 | 0.14 ± 0.01 |
| FA/protein/ polysaccharide | 0.25 | | 181 ± 1 | 0.17 ± 0.01 |
| FA/protein/ polysaccharide | 0.5 | | 177 ± 2 | 0.14 ± 0.01 |

Example 5

Protection of Folic Acid from UV Degradation in Folic Acid/Soy Protein/Soy Polysaccharide Nanogels As mentioned above, folic acid is sensitive to UV radiation. Because of intramolecular fluorescence quenching, folic acid has an extremely low fluorescence quantum yield, approximately 0.005. Pterins, which is formed after the cleavage of the C9-N10 bond in the folic acid molecule, has an increased fluorescence peak around 445 nm. The fluorescence quantum yield of 6-formyl pterin (FPT) is nearly 0.1 and that of pterin-6-carboxylic acid (PCA) is about 0.2. The fluorescence in the region of 445 nm increases with the formation of FPT as a result of the C9-N10 bond cleavage followed by the photo-induced conversion of FPT to PCA [M. K. Off et al., Journal of Photochemistry and Photobiology B: Biology 80 (2005) 47-55].

The UV degradation of folic acid was investigated in this study. The folic acid/protein/polysaccharide nanogel solution at pH 4.0 containing 0.25 or 0.5 mM folic acid was placed in a 7 ml glass bottle at a distance of 30 cm from a UV radiometer (500 w, peak A=365 nm) for 1 h. Individual folic acid dissolved in 10 mM pH 7.4 phosphate buffer with FA concentration of 0.25 or 0.5 mM was also investigated. The mixture of 5 mg/ml protein and 0.25 mM folic acid at pH 7.4, and the mixture of 15 mg/ml polysaccharide and 0.25 mM folic acid at pH 7.4 were also investigated. After the UV radiation, the folic acid/protein/polysaccharide nanogel solution was adjusted to pH 7.4 to release folic acid. The released folic acid in the solution was isolated by ultrafiltration and was analyzed as described below. After 10 and 20 times dilution for 0.25 and 0.5 mM folic acid, respectively, the 450 nm fluorescence intensity of the ultrafiltrate excited at 348 nm was measured. All the samples for investigation of folic acid degradation do not contain any sodium azide.

Table 3 shows folic acid fluorescence intensity ratio before and after the UV radiation. For individual folic acid solution, after the UV radiation, the fluorescence intensity at 450 nm increases 89 and 85 times when folic acid concentration was 0.25 and 0.5 mM, respectively. The average 87 times of the increase for the fluorescence intensity after the UV radiation indicates the degradation of the folic acid inside the glass bottle. Increasing folic acid concentration from 0.25 to 0.5 mM does not influence the degradation significantly. Although individual protein can only bind about 10% of the folic acid and individual polysaccharide cannot bind with folic acid at pH 7.4 (Table 1), the result in Table 3 shows that the individual protein and individual polysaccharide can reduce folic acid degradation greatly. Compared with the individual folic acid, the degradation of folic acid reduces to 30% and 22% in the presence of polysaccharide and protein at pH 7.4, respectively. Folic acid/protein/polysaccharide nanogels can effectively protect the folic acid from the degradation at pH 4.0; only 12% of the loaded folic acid was degraded after the same UV radiation. We also investigated the folic acid/protein/polysaccharide nanogels after 1 month storage; the folic acid fluorescence intensity does not change after the folic acid was released and isolated, compared with the fresh prepared folic acid/protein/polysaccharide nanogels. The released and isolated folic acid from folic acid/protein/polysaccharide nanogels was radiated by UV light. After the same radiation, the folic acid fluorescence changed as the folic acid solution prepared at pH 7.4 directly. This result further demonstrates that folic acid/protein/polysaccharide nanogels can effectively protect the folic acid from the UV degradation at pH 4.0.

TABLE 3

Degradation degree of folic acid (FA) in different samples after UV radiation. The degradation degree was obtained by measuring 450 nm intensity of folic acid fluorescence emission spectra before and after the UV radiation. The folic acid was released at pH 7.4 and isolated via ultrafiltration. The fluorescence excitation wavelength was 348 nm.

| Sample | FA concentration in feed (mM) and UV radiation pH | $I_{UV}/I^{1)}$ | Degradation degree (%) |
|---|---|---|---|
| FA | 0.25, pH 7.4 | 89 ± 3 | 100 |
| FA | 0.5, pH 7.4 | 85 ± 2 | 100 |

TABLE 3-continued

Degradation degree of folic acid (FA) in different samples after UV radiation. The degradation degree was obtained by measuring 450 nm intensity of folic acid fluorescence emission spectra before and after the UV radiation. The folic acid was released at pH 7.4 and isolated via ultrafiltration. The fluorescence excitation wavelength was 348 nm.

| Sample | FA concentration in feed (mM) and UV radiation pH | $I_{UV}/I^{1)}$ | Degradation degree (%) |
|---|---|---|---|
| Polysaccharide + FA | 0.25, pH 7.4 | 27 ± 4 | 30 ± 5 |
| Protein + FA | 0.25, pH 7.4 | 20 ± 2 | 22 ± 3 |
| FA/protein/polysaccharide nanogels | 0.25, pH 4.0 | 11 ± 1 | 12 ± 1 |
| FA/protein/polysaccharide nanogels | 0.5, pH 4.0 | 9 ± 2 | 11 ± 2 |

1)The ratio of FA fluorescence intensity after UV radiation to the intensity before UV radiation.

Example 6

Folic Acid/Pea Protein/Soy Polysaccharide Nanogel Preparation and Protection of Folic Acid from UV Degradation Pea protein was dissolved in water and the pH was adjusted to pH 3.25. After overnight equilibrium, the solution was centrifuged at 5000 rpm for 30 minutes to remove unsolved protein. The supernatant contained 15 mg/ml pea protein. Folic acid/pea protein/soy polysaccharide nanogels were prepared by mixing soy polysaccharide solution with folic acid solution and pea protein solution at pH 7.4 under stirring. In the mixture, the final pea protein concentration was 5 mg/ml, polysaccharide concentration 15 mg/ml, folic acid concentration 0.25 mM, and the volume was 25 ml. The pH of the mixture was adjusted to 4.0, after 3 h stirring, the pH was adjusted to 4.0 again. The mixture was homogenized by high pressure homogenization at 600 bar for 2 min and then was heated at 90° C. for 1 h to obtain folic acid encapsulated pea protein/soy polysaccharide nanogels. The resultant nanogels have a size 203 nm and PDI 0.23 (Table 5).

The UV degradation of folic acid was investigated. Compared with the individual folic acid, the degradation of folic acid reduces to 19% in the presence of pea protein (Table 4). Folic acid/pea protein/polysaccharide nanogels can effectively protect the folic acid from the degradation at pH 4.0; only 13% of the loaded folic acid was degraded after the same UV radiation.

TABLE 4

Degradation degree of folic acid (FA) in different samples after UV radiation. The degradation degree was obtained by measuring 450 nm intensity of folic acid fluorescence emission spectra before and after the UV radiation. The folic acid was released at pH 7.4 and isolated via ultrafiltration. The fluorescence excitation wavelength was 348 nm.

| Sample | FA concentration in feed (mM) and UV radiation pH | $I_{UV}/I^{1)}$ | Degradation degree (%) |
|---|---|---|---|
| FA | 0.25, pH 7.4 | 91 | 100 |
| FA/pea protein nanogels | 0.25, pH 4.0 | 17.5 | 19 |
| FA/pea protein/polysaccharide nanogels | 0.25, pH 4.0 | 11.5 | 13 |

1)The ratio of FA fluorescence intensity after UV radiation to the intensity before UV radiation.

Example 7

Stability of Folic Acid/Pea Protein/Soy Polysaccharide Nanogel Solution and Folic Acid/Soy Protein/Soy Polysaccharide Nanogel Solution at pH 3.0, 3.5, and 4.0, and Redispersion Ability of the Nanogels after Frozen Dry Folic acid/pea protein/soy polysaccharide nanogel solution and folic acid/soy protein/soy polysaccharide nanogel solution prepared at pH 4.0 were changed to pH 3.5 and 3.0, separately, to investigate the stability. The data in Table 5 show that the nanogel sizes do not change after one week storage in pH 3 and 3.5 media, indicating the nanogels are stable in beverage pH condition. Furthermore, the nanogels were frozen dry and then re-dispersed in water. After re-dispersion, the nanogel sizes do not change significantly, suggesting the nanogels can be stored and used in dry powder form.

TABLE 5

DLS results of folic acid/pea protein/soy polysaccharide nanogels and folic acid/soy protein/soy polysaccharide nanogels in pH 3.0, 3.5, and 4.0 media, and re-dispersion after frozen dry at pH 4.0 medium. The folic acid concentration was 0.25 mM.

| Sample | | Solution pH | Dh (nm) | PDI |
|---|---|---|---|---|
| Fresh prepared | FA/soy protein/ polysaccharide | 4.0 | 170 | 0.11 |
| | | 3.5 | 173 | 0.15 |
| | | 3.0 | 177 | 0.16 |
| | FA/pea protein/ polysaccharide | 4.0 | 203 | 0.23 |
| | | 3.5 | 204 | 0.19 |
| | | 3.0 | 207 | 0.19 |
| After one week storage | FA/soy protein/ polysaccharide | 4.0 | 174 | 0.15 |
| | | 3.5 | 172 | 0.21 |
| | | 3.0 | 174 | 0.18 |
| | FA/pea protein/ polysaccharide | 4.0 | 204 | 0.23 |
| | | 3.5 | 202 | 0.23 |
| | | 3.0 | 201 | 0.20 |
| After frozen dry and redispersion | FA/soy protein/ polysaccharide | 4.0 | 186 | 0.18 |
| | FA/pea protein/ polysaccharide | 4.0 | 206 | 0.16 |

The invention claimed is:

1. A nanogel composition comprising nanoparticles comprised of:
    a) 0.1 to 5 weight-% based on the dry weight of the composition of at least one water-soluble active ingredient selected from the group consisting of ascorbic acid, biotin, folic acid, nicotinic acid, thiamine, and vitamin B6;
    b) 9 to 40 weight % based on the dry weight of the composition of at least one plant protein selected from the group consisting of food-grade proteins derived from soy, lupin, pea and potato plants; and
    c) 50 to 90 weight-% based on the dry weight of the composition of at least one soy soluble polysaccharide; wherein
    the at least one protein and the at least one soy soluble polysaccharide are present in a weight ratio of the plant protein to the soy soluble polysaccharide, based on weight of the nanogel composition in dry matter, is between 1:1 and 1:6.

2. The nanogel composition according to claim 1, wherein the water-soluble active ingredient is folic acid.

3. The nanogel composition according to claim 1, wherein the at least one plant protein is selected from the group consisting of soy protein and pea protein.

4. The nanogel composition according to claim 1, wherein the nanoparticles have an average particle size between 120 and 250 nm as measured by dynamic light scattering.

5. A process for the manufacture of a stable nanogel containing at least one water-soluble active ingredient selected from the group consisting of ascorbic acid, biotin, folic acid, nicotinic acid, thiamine, and vitamin B6, wherein the process comprises the following steps:
- I) mixing in water, at least one or more soy soluble polysaccharides, at a pH of about 7.4, a solution comprising at least one water soluble active ingredient selected from the group consisting of ascorbic acid, biotin, folic acid, nicotinic acid, thiamine, and vitamin B6, and a solution of a plant protein, wherein the protein is at a concentration in the solution of 1 to 10 g/L, and wherein the plant protein and the soy soluble polysaccharide are present at a weight ratio of 1:1 to 1:6, and wherein the concentration of the water-soluble active ingredient in the solution is between 0.001 to 0.2 g/L;
- II) optionally stirring the mixture of step I) for 1 minute to 8 hours,
- III) adjusting the pH of the mixture from step I) or II) to pH around 4, and repeating the pH adjustment after 2 to 3 hours;
- IV) homogenizing the mixture of step III) followed by heating the homogenized mixture at a temperature of 90° C. for 1 hour to form a nanogel;
- V) heating the nanogel at a temperature between 70 to 95° C. for at least 45 minutes, and
- VI) optionally drying the resulting nanogel of step V).

6. The process according to claim 5, wherein the concentration of the plant protein is from 4 to 6 g/l.

7. The process according to claim 5, wherein the weight ratio of protein to polysaccharide is from 1:2 to 1:4.

8. The process according to claim 5, wherein the concentration of active ingredient is between 0.01 and 0.15 g/l.

9. A nanogel obtained by the process according to claim 5.

10. The nanogel according to claim 9, wherein the plant protein is soy protein or pea protein, and wherein the active ingredient is folic acid.

11. An enriched and/or fortified food, beverage, animal feed or cosmetics composition which comprises the nanogel composition according to claim 1.

12. A process for the manufacture of a beverage comprising the step of mixing the nanogel composition according to claim 1 with a water-based beverage.

13. A beverage obtained by the process according to claim 12.

14. The beverage according to claim 13, wherein the beverage has a pH of between 3 and 5.5.

* * * * *